United States Patent
Falk-Jordan et al.

(10) Patent No.: US 8,277,761 B2
(45) Date of Patent: Oct. 2, 2012

(54) CHANNELLESS FLUIDIC SAMPLE TRANSPORT MEDIUM

(75) Inventors: Stefan Falk-Jordan, Waldbronn (DE); Patrick Kaltenbach, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 592 days.

(21) Appl. No.: 12/377,179

(22) PCT Filed: Aug. 3, 2006

(86) PCT No.: PCT/EP2006/065047
§ 371 (c)(1),
(2), (4) Date: Jun. 15, 2009

(87) PCT Pub. No.: WO2008/014825
PCT Pub. Date: Feb. 7, 2008

(65) Prior Publication Data
US 2009/0266713 A1   Oct. 29, 2009

(51) Int. Cl.
*G01N 27/447* (2006.01)
(52) U.S. Cl. .......... 422/527; 422/82.05; 422/82.08; 204/601; 204/622; 204/624; 427/264
(58) Field of Classification Search .......... None
See application file for complete search history.

(56) References Cited

U.S. PATENT DOCUMENTS

| 5,736,188 A | 4/1998 | Alcock et al. |
|---|---|---|
| 6,376,231 B1 | 4/2002 | Enomoto et al. |
| 6,509,085 B1 | 1/2003 | Kennedy |
| 2003/0016075 A1 | 1/2003 | Itoh |
| 2003/0059929 A1 | 3/2003 | Heller et al. |
| 2003/0127333 A1* | 7/2003 | Lauks et al. ............ 204/600 |
| 2004/0180130 A1 | 9/2004 | Wixforth |
| 2005/0074898 A1* | 4/2005 | Datwani et al. ............ 436/180 |

FOREIGN PATENT DOCUMENTS

| EP | 1217368 | 6/2002 |
|---|---|---|
| WO | WO 99/22228 A1 | 5/1999 |
| WO | WO 03008977 A2 | 1/2003 |
| WO | 03/016075 | 2/2003 |
| WO | WO 2004/050243 A1 | 6/2004 |

OTHER PUBLICATIONS

International Search Report dated Aug. 3, 2006.
Written Opinion dated Aug. 3, 2006.

\* cited by examiner

*Primary Examiner* — In Suk Bullock
*Assistant Examiner* — Timothy G Kingan

(57) ABSTRACT

A fluidic device (100) comprising a substrate (101) and a transport medium (103) provided on the substrate (101) to define a transport path for transporting a fluidic sample (104) driven by an electric force.

11 Claims, 2 Drawing Sheets

CHANNELLESS FLUIDIC SAMPLE TRANSPORT MEDIUM

This application is the National Stage of International Application No. PCT/EP2006/065047, filed on 3 Aug. 2006 which designated the United States of America, and which international application was published as Publication No. WO 2008/014825.

BACKGROUND ART

The present invention relates to fluidic devices.

In microstructure technology applications, fluid may be conveyed through miniaturized channels (which may be filled with gel material) formed in a substrate. For a capillary electrophoresis device as an example for such a microstructure technology application, it may be necessary to generate an electric field in the fluid channels in order to allow for a transport of components of the fluid through the channels using electric forces. Such an electric force or field may be generated by dipping contact pins of the capillary electrophoresis device into the fluid which may be filled in a well defined by a carrier element coupled to a microfluidic chip, and by applying an electrical voltage to such contact pins.

U.S. Pat. No. 6,509,085 B1 discloses to provide laminates having channel structures disposed between sheets of the laminate. The channels are raised on a sheet of laminate, typically by printing the structure on the sheet.

U.S. Pat. No. 5,736,188 discloses a backing sheet provided with a pattern of pathways of silica or cellulose by a printing process. There may be multiple pathways leading from an eluant application region meeting in a merged zone to a detection zone and thence to a waste reservoir. Different pathways may have different fluid traversal times because they differ in length and/or material. Thus analyte and reagents deposited at depots on different pathways are sequentially delivered (by capillary forces, that is to say be a purely internal force) to the detection zone. Reagents may be applied by printing. The detection zone may have an electrode assembly, also applied by printing, for detecting the effects of analyte.

DISCLOSURE

It is an object of the invention to enable a simplified manufacture and/or operation of a fluidic device. The object is solved by the independent claims. Exemplary embodiments are shown by the dependent claims.

According to an exemplary embodiment of the invention, a fluidic device is provided comprising a substrate (for instance a glass slide) and a transport medium (for instance a gel) provided (for instance printed) on the substrate to define a transport path for transporting a fluidic sample (for instance a biochemical liquid to be analyzed) driven by an external source (for example an electric force by applying an electric voltage to electric contact pins to be coupled electrically to the transport medium in an electrophoresis application).

According to another exemplary embodiment, a method of manufacturing a fluidic device is provided, the method comprising providing a transport medium on a substrate of the fluidic device to form a transport path for transporting a fluidic sample driven by an external (for instance electric) force.

The term "external force" may particularly denote any driving mechanism which is not intrinsically based on the material of the fluid transport medium (like pure capillary forces) but which results of an influence of a force promoting component which is provided externally of or apart from the fluid transport medium. For instance, a mechanical (for example vacuum or pressure) force generator (like a pump) or an electrical force generator (like electrodes connected to a voltage supply) may be used to generate such an external force.

According to an exemplary embodiment, a transport medium like gel for a gel electrophoresis device may be directly deposited onto a for instance completely or partially planar surface of a substrate, thereby making it dispensable to provide complex fluidic structures within a surface portion of the substrate. In contrast to this, material may simply be sputtered, printed, deposited, spotted or adhered onto a surface of a substrate, thereby forming a fluidic device having elevated structures as fluid transport structures. The transport medium may be or may be not formed as one or more "elevated structures".

Electric forces acting on components of a fluidic sample flowing through the transport medium may be applied to such a deposited transport medium, for instance by dipping or pressing electrodes into specific portions of the transport medium path or by forming the transport medium on top of electrode structures formed in and/or on the substrate, thereby allowing a motion of components of a fluidic sample under the influence of such an externally applied electric force. The manufacture of such a fluidic device is very simple and may also allow to provide three-dimensional layer structures for complex or sophisticated fluid transports.

Therefore, a process and an apparatus for micro- and nanoscale measurements, particularly for life science chip technology, may be provided. In contrast to the conventional need to form channels in a substrate for micro- and nanotechnology applications which channels then have to be filled with gel material or the like before use by a user, exemplary embodiments may require significantly less effort in manufacture and operation and may be manufacturable with less costs. In contrast to the manufacture of a complex channel system in which corresponding substances may be filled and which substances may be electrically contacted afterwards, exemplary embodiments may allow to simply print structures (like gel, dye, buffer, sample, etc.) even on a completely planar substrate. A fluidic sample may then be conducted under the influence of an external force through the elevated structure as the transport medium (for example an electric force, additionally mechanical forces generated by a pressure/vacuum, magnetic forces generated by magnets, etc. may be generated as well).

Particularly, using print technologies like the ink-jet technology, varnishing technologies, dispenser technologies (for instance adhering technology), pen-like material application technologies (for instance "painting" on a substrate surface with gel material), stamp technologies, or serigraphy, it may be possible to design a fluid transport structure by deposition without the need to make use of channel walls of the substrate (which may be planar or which may be non-planar, as desired) as a mechanical support. The height of the fluid transport medium in a vertical dimension can be adjusted by repeating the deposition procedure once or several times. Exemplary embodiments may have applications in the pico-, nano- and microtechnology.

The deposition and design of the elevated structures in a multilayer procedure may be performed in a similar manner as with rapid prototyping known from plastic technology.

According to exemplary embodiments, it is possible to combine fixed structures with variable structures. Components like electric contacts and a basis may be fixed. The active functional structure of a separation technology (for instance gel for gel electrophoresis separation) may be a variable structure which can be adjusted for a specific application. The entire design of a chip adapted for a specific application can be realized in a modular manner as some kind of construction set, in which different modules are available which can be combined in a flexible, user-defined and variable manner.

By such a procedure, it may also be possible to integrate elements of process technology (for instance using valves, pumps and/or other microtechnology components). The chip technology (wherein chip may particularly denote a chip in the field of application of life science) may thereby be brought to a highly integrative level.

Since very thin layers may be applied (for instance with atomic layer deposition, ALD), the thickness of the layers may be controlled with an accuracy of up to one atomic layer), exemplary embodiments may be used in the field of microtechnology, nanotechnology, and even picotechnology.

An electrical connection element or an electrical supply can be formed by depositing electrically conductive structures prior to (or after) the process of forming the transport medium. This may even allow depositing active electric members, for instance a capacitive measurement system, on a substrate. Particularly, when foreseeing such a chip as reusable (for instance by removing the deposited transport medium after use without removing deposited electrode structures, for instance for such a capacitive measurement system), the costs for such a system may be reasonable. However, it is also possible that electric supplies or other electrical components can be manufactured after manufacturing the transport medium.

The substrate may comprise one or a plurality of active zones (for instance portions having specific affinities), sensors, different temperature zones, etc., and the microfluidic structure may be simply printed on the substrate.

For pressure conduits, vacuum conduits and other supply lines of gas or liquids (that is to say fluids), a part of the transport structures may also be manufactured inside of the substrate prior to the ink-jet process or other deposition process.

In order to suppress or avoid undesired drying of the transport medium during or after manufacture, it is possible to perform the manufacture process or operate the device in a saturated steam atmosphere.

After depositing the transport medium (for instance gel) structure, it is possible to cover the substrate with a protection layer (for instance varnish). By taking this measure, a closed layer may be generated, and also a closed fluid path guide.

When using an ink-jet technology, it may be possible to design very different zones on the chip, for instance comprising gel and dye, only gel, gel with additives, or any other fluids and/or solids.

By such a deposition technique, it may also be possible in an easy manner to manufacture fluidic crossings or bifurcations of transport medium conduits (for instance for mixing fluids, promoting a chemical reaction between fluids, etc.), as well as three-dimensional structures.

Exemplary embodiments may also be implemented in the context of a multilayer technology. For instance, a layer may first be deposited which modifies or adjust the surface properties. After such a conditioning procedure, a patterned layer with the transport medium may be deposited. It is also possible that multiple structures of the transport medium are deposited (next to one another on the substrate surface or vertically stacked). It is also possible to design multiple tube structures.

Instead of a varnish, it is also possible to provide a cover element which comprises a spacer which may seal the chip and form wells. Into such wells, the samples and contacts may then be immersed or dipped.

Such a technology can be used to manufacture multi-purpose ready-to-use chips as well as to manufacture chips which are printed on the client side ("chip-on-demand"). According to an exemplary embodiment, it is possible to provide a chip on demand, or in other words to have it printed right before use at a costumer side. This may also include the possibility that the customer can design her or his own chip-layouts.

Surface portions of the carrier substrate and/or of the cover element can (at least partially) be formed of hydrophobic material so that the surface portions on which the transport medium shall be deposited may be spatially defined.

The substrate and/or the cover may be configured to be reusable. Recycling used fluidic devices may reduce costs for the analysis.

It is also possible to manufacture transport medium structures having a valve function, wherein such a valve may be operated by a variation of the temperature (for instance a part of the printed structures may be freezed or heated).

Pre-printed and (subsequently) freezed structures are shippable easily, and can be conditioned for use by melting.

According to an exemplary embodiment, a fluid transport content, that is to say a transport medium for a fluidic sample, may be applied on a carrier for a chip, particularly for electrophoresis applications. Such a fluid path content may be a gel which may be deposited in a channelless manner on a surface of a life science chip. Such a fluidic sample may be driven to be moved using an external (electric) energy, particularly using the principle of (gel) electrophoresis. Additionally or alternatively to an electrophoretic separation, other separation forces like vacuum might be applied (for example evaporation driven separation as disclosed as such, for instance, by Manz et al.).

According to an exemplary embodiment, a gradient gel may be applied on a substrate, for instance using two or more printing nozzles with spatially modifiable mixture ratio of the components emitted by the printing nozzles.

A substrate having holes or being free of holes may be used, and fluid path structures may be printed onto the substrate (for instance gel material may be printed thereon). The holes may serve as fluid containers but may be partially or entirely filled with fluid transport medium.

If desired, such a structure may be covered with a protection varnish so as to protect the printed structure for the time between manufacture and actual use. Instead of providing a protection varnish, the substrate with the deposited transport medium may be shock-freezed so as to avoid or delay drying or other deterioration of the transport medium. In the latter embodiment, a passivation layer, for instance made of varnish, may be omitted. A further alternative is a dried structure of transport medium deposited on a substrate which dried structure can be humidified directly before use, to condition the chip for a biochemical application.

The substrate may be made of any desired material, like glass, silicon, plastic, ceramics, semiconductor or the like.

The transport medium may be foreseen to be in functional contact with small (fluid) containers/recesses formed in the substrate or with connections for providing an electric contact.

After having deposited a passivation layer over the elevated transport medium structure, the surface can be planarized or may remain non-planar.

A substrate with a gel deposited thereon and a passivation layer of varnish applied thereon may be a unit which can be conditioned for an actual experiment by removing the passivation selectively from the portions of the substrate covered with the transport medium. For this purpose, it is possible, for example, to put a caddy or any other carrier element on top of the chip, wherein the caddy may have one or more cutting elements or tips for penetrating or destroying specific portions of the varnish, to thereby expose an "active" surface of the chip, namely at least a portion of the surface of the substrate which is covered with the transport medium.

As an alternative to such a tip, it is possible to foresee the varnish of a material which can be automatically removed when brought in contact with an aqueous solution. Thus, it is possible to manufacture the varnish from a water-soluble material. In such a scenario, the entire surface of the varnish or specific surfaces of the varnish are sacrificed when being contacted with a sample to be analyzed, thereby exposing the transport medium to the fluidic sample, allowing to bring the fluidic sample in fluid communication with the transport medium.

For example, a transport medium line printed on a substrate may have a thickness between 10 μm and 25 μm. A varnish layer may have a dimension in the order of magnitude of 1 μm. For example, a silicone varnish may be used as a passivation layer, or a water-soluble varnish.

As a further alternative, it is possible to cover the substrate with the deposited transport medium structures by a foil. Such a foil may then be removed by a user before use of the device. The foil may be perforated or manufactured otherwise in such a manner that when removing the foil, only selective portions of the substrate surface, particularly the surface portions which are covered with the transport medium, are exposed.

In many cases, alignment markers are manufactured on microfluidic chips allowing a proper alignment between different substrate layers to be connected to one another for forming such fluidic chips. Such alignment markers may also be printed on or deposited otherwise on a surface of the substrate, for instance during the same procedure during which the transport medium structures are provided. This may allow to simplify manufacture. When the alignment markers shall be optically visible, it is also possible to mix the material for the transport medium with a dye for application of the mixture on the substrate as the alignment markers.

According to an exemplary embodiment, a hydrophobic/hydrophilic pattern may be applied or deposited on the substrate, thereby enabling a fluidic sample to be present only in specific portions of the surface of such a substrate. Also the Lotus effect may be taken into account for defining surface portions which shall be deposited with the fluidic sample, and surface portions which shall remain free of the fluidic sample. By providing microstructures with special dimensions on the surface, the fluid repellant property as known from the Lotus plant may be used.

Wells may be formed in a caddy structure which can be provided centrally or laterally on a chip. Therefore, via such wells, a fluidic sample may be filled in the microfluidic chip device. Metallic contacts (like pins) for electrically contacting the transport structures so as to generate an electric or electromagnetic force driving the fluidic sample through the transport medium may be provided on a main surface of the substrate, or may be also foreseen at lateral contact areas of the substrate. Particularly when a cover element is put on top of a substrate on which the transport medium has been deposited, the resulting device may also be suitable for pressure-driven or vacuum-driven applications (or any other external force), like pressure-driven liquid chromatography separation applications. For this purpose, a pressure may be applied to end portions of the transport medium, thereby forcing a fluidic sample to move through the transport medium.

According to exemplary embodiments, it may also be possible to manufacture "negative" structures. For such a purpose, sacrificial transport medium layers may be applied to the substrate and may be passivated by a varnish. Afterwards, the sacrificial material may be removed, for instance by evaporating them through the cover layer as a consequence of an appropriate thermal treating.

It may be advantageous that the substrate and/or the transport medium is optically transparent, particularly for optical detection methods like fluorescence detection. For example, the carrier may be a substrate made of glass, quartz, or PMMA or any other polymer (which may have a small optical background).

Therefore, according to an exemplary embodiment, a ready-to-use chip may be provided on which a user does not have to insert manually gel material in a complex channel structure but use a readily manufactured fluid transport structure which is already pre-printed on a surface of the substrate. It may be dispensible that the user has to condition the transport medium for use (for instance by humidifying it, or by selectively removing portions of a passivation layer covering the transport medium).

Exemplary embodiments may use containers or samples in the dimension of picoliters, nanoliters, microliters, or milliliters.

The transport medium may be formed by any deposition procedure or by any printing procedure. For instance, ink-jet, bubble jet, serigraphy, nozzle deposition, rollerball deposition with a two-dimensional scanning on a surface substrate, or the generation of hydrophilic/hydrophobic patterns may be implemented. After having manufactured hydrophilic/hydrophobic patterns by printing or any other procedure, it may be dipped into an emersion bath. For instance, a fluid of the emersion bath may only remain on hydrophilic portions of such a pattern.

It is also possible to provide transport medium based valves for switching between different fluid path configurations. For this purpose, a swellable substance may be provided on the substrate, bridging two transport medium conduits when the swellable substance is in a swollen operation mode, and disconnecting the structures when the swellable substance is in a non-swollen operation mode. As an alternative to a moisture-based expansion, a temperature-based expansion or compression may be realized.

According to an exemplary embodiment, a lab-on-chip may be formed in which different procedural components like mixing of samples, reaction, separation, etc. may be combined on a single fluidic chip.

Next, further exemplary embodiments of the fluidic device will be explained. However, these embodiments also apply to the method for manufacturing a fluidic device.

It is possible that the transport medium comprises a non-trenched wall. The term "non-trenched wall" may particularly denote a wall which is not defined entirely by a trench formed in a substrate, but which is defined by the transport medium itself. At least a part of the lateral wall of the transport medium may be free of an external mechanical support, and may be supported by the intrinsic material properties of the transport medium (for instance being in a gel-like phase). Therefore, the transport medium may comprise a channelless wall, that is to say a wall which does not necessarily need a side wall of a channel formed in the substrate for mechanical support.

However, it is possible that at least a part of the transport medium is deposited in a channel structure. At least of the lateral portion between the transport medium and the surrounding channel structure may be free from a direct contact or mechanical support between the transport medium and the surrounding channel structure.

The transport medium may be free of a lateral mechanical support by the substrate along at least a part of a lateral wall of the transport medium. Such an at least partially channelless wall may be defined by an edge portion of the transport medium itself. For instance, a material property, for instance viscosity, of the transport medium itself may be selected and adjusted in such a manner that, when being deposited on the substrate, the edge portion remains mechanically stable and does not distribute the material of the transport medium over the entire surface of the substrate. Therefore, a self-supporting structure may be formed as the transport medium.

The channelless wall may be formed independently of a sub-surface trench in the substrate. Therefore, even if a trench is formed in the substrate, lateral side walls of this trench do not define or limit the lateral extension of the transport medium.

At least one recess may be formed in the substrate and may be in fluid communication with the elevated transport medium conduits. Such recesses may be fluid containers or buffer containers or waste containers which may supply the transport medium with fluidic sample or other components.

According to an embodiment, the transport medium may be in a dried state and may be foreseen to be humidified before being capable of transporting the fluidic sample. By drying the transport medium, the storage of the fluidic device for a long time between manufacture and actual use may be made possible. Consequently, the fluidic device may be delivered to a client "ready to use", and the client may activate the fluidic device for an actual experiment with low effort, simply by contacting a surface of the fluidic device with water, an aqueous solution or into a water vapor saturated environment to humidify the dried transport medium.

Additionally or alternatively, a passivation layer may cover at least a part of the transport medium. Such a passivation layer may mechanically protect the transport medium against an environment, and may avoid drying of the transport medium. The passivation layer may comprise at least one material of the group consisting of a varnish, silicone and a water-soluble material. Such a passivation layer may be selectively removed or destroyed for exposing an active surface of the fluidic device.

The fluidic device may comprise a carrier element having a well. The carrier element may be adapted to be connected to the substrate in a manner to enable external access to the transport medium through the well. The well may then allow a needle or a pipette or any other fluid emitting tip to insert a fluidic sample to be brought in contact with the transport medium. Such a well may have the shape of a hollow cylindrical structure in a plate defining a path along which the fluid to be supplied to the transport medium is brought in contact with the surface of the fluidic device. However, the use of such a carrier element or caddy is merely optional, and a carrier element may be omitted according to exemplary embodiments. For instance, a removable foil may be provided on a chip. When removing the foil, selective portions of the chip may be exposed. Such exposed portions may then be provided with a drop of sample, buffer, or the like.

The carrier element may comprise one or more tips (for instance a cutting element) located and designed to penetrate through the passivation layer in an operation state in which the carrier element is connected to the substrate. Therefore, when a user clicks a carrier element onto the fluidic device to make the fluidic device ready for an experiment, the tip may automatically penetrate the passivation layer so as to expose the transport medium.

Alternatively, the passivation layer may be configured to be automatically removable when the passivation layer is brought in contact with a fluid, for instance when a fluidic sample is filled in the well.

Further alternatively, a removable foil may be provided covering the substrate and the transport medium. The foil may be adapted to selectively expose at least one surface portion of the transport medium when removing the foil. Therefore, a plastic foil which can be removed and which has perforated and adhering surface portions may define portions of the surface which can be exposed by removing the foil, and other surface portions which remain covered by the foil, so that the foil can still fulfill its protecting function at the remaining portions. Even more simple, a detachable and even reusable cover element may be provided.

At least one alignment marker may be provided on the substrate and may comprise the same material as the transport medium. This may enable to manufacture alignment markers and the fluid conduits in one common manufacturing procedure. Since the alignment marker may be used for optically aligning the substrate with respect to another substrate (for instance when manufacturing a multi-substrate comprising fluidic device), it may be advantageous that the alignment material additionally comprises a dye material. For example, the alignment marker may then be a gel to which dye material is added.

The transport medium may comprise at least two portions separated from each other by a swellable material which, in a first operation state, enables a fluid communication between the at least two portions via the swellable material, and, in a second operation state, disables a fluid communication between the at least two portions via the swellable material. Such a swellable material which may be swollen by a thermic or a fluidic trigger scheme. It may serve as a fluidic valve for selectively connecting or disconnecting different conduits formed by the transport medium. Therefore, a switch between different fluid path configurations is possible.

The transport medium may adhere to the substrate, so that the fluidic device is very stable and robust. Thus, the transport medium and the substrate may be configured so that a bonding or stable connection between the transport medium and the substrate is enabled. For instance, forming micro-elevations of electrophoresis gel material on a glass substrate is a good combination.

The transport medium may be adapted for transporting the fluidic sample driven by an externally applicable electric force. Such an electrical force may be applied by a voltage supply unit supplying contacts to be brought in physical and electrical contact with the transport medium with electric energy. In other words, electric fields may be generated within the deposited transport medium.

The fluidic device may comprise one or more electric contacts to be connected to the transport medium. Such a contact may be formed directly on or embedded in the substrate before depositing the transport medium. This may allow to simply wash off the transport medium after use to recycle the fluidic device. Then, the electric contacts may be used again, and new transport medium material may be deposited on the contacts again.

Alternatively, such electric contacts may be provided as separate components (like pins) and may be dipped into the transport medium or may be provided or dipped in recesses formed as fluid containers.

The transport medium may comprise a gel material, particularly a gradient gel material. A gradient gel may be used for electrophoresis applications and may gradually modify the chemical properties of the gel along an extension of a fluidic conduit, thereby allowing to selectively separate or immobilize different fractions of a fluidic sample within a gel strip.

The fluidic device may be adapted as a fluidic chip device. In other words, the components of the (life science) fluidic chip may be provided on and/or in the chip-like substrate, for instance a glass substrate. This may allow for a miniature manufacture of the fluidic device.

Particularly, the fluidic device may be adapted as a fluid separation device. Therefore, different components of a fluid may be separated when being transported under the influence of an external electric field or force along the transport medium structures.

Particularly, the fluidic device may be adapted as an electrophoresis device. The field of electrophoresis may denote the separation of different components of a fluidic sample due to different affinities between components of the sample and a chemical environment and due to different electrical charge properties of components of the sample in a surrounding chemical environment, like a gel.

The fluidic device may be adapted as a microfluidic device. The term "microfluidic device" may particularly denote a fluidic device as described herein which allows to convey fluid through micropores, that is pores having a dimension in the order of magnitude of micrometers or less.

The fluidic device may further be adapted as a nanofluidic device. The term "nanofluidic device" may particularly denote a fluid device as described herein which allows to convey fluid through nanopores, that is pores having a dimension in the order of magnitude of nanometers or less.

The fluidic device may also be adapted as a picofluidic device. The term "picofluidic device" may particularly denote a fluidic device as described herein which allows to convey fluid through picopores, that is pores having a dimension in the order of magnitude of picometers.

The fluidic device may be adapted to transport a fluidic sample comprising at least one of the group consisting of antibodies, a chemical and/or biological relevant substance, and a dye. Thus, the fluid may also comprises, for instance, a mixture (or pure part) with ladder, antibodies, chemical relevant substances, dyes, etc.

The fluidic device may further comprise at least one channel formed in the substrate for channeling the fluidic sample. Therefore, even if the transport medium is applied by deposition or printing techniques to a surface of the substrate, it is nevertheless possible that at least a part of the transport medium is provided within channels, however still having the capability due to its intrinsic material properties to be supported in a self-employed manner. In other words, lateral walls of such a channel may be not essential or do not contribute to the lateral definition and stability of the transport medium.

The fluidic device may comprise at least one fluid path formed in the substrate and filled with the transport medium for channeling the fluidic sample, wherein the at least one fluid path may be in fluid communication with the transport medium provided on the substrate. By such a configuration, fluid communication between transport medium portions out of fluid paths and transport medium portions within a fluid path may be made possible.

The substrate may comprise an optically transparent material to enable optical detection of separated components, for instance to detect different spatially separated bands of fractions of a sample in an electrophoresis strip. Such a substrate may comprise a glass, a quartz, or a plastics material like PMMA.

The fluidic device may be adapted to analyze at least one of the group consisting of a physical, a chemical and a biological parameter of at least one component of the fluidic sample. The term "physical parameter" may particularly denote a size or a temperature of the fluidic sample. The term "chemical parameter" may particularly denote a concentration or a fraction of the analyt, an affinity parameter, or the like. The term "biological parameter" may particularly denote a concentration of a protein, a gene or the like in a biochemical solution, a biological activity of a component, etc.

The fluidic device may comprise at least one of a sensor device, a device for chemical, biological and/or pharmaceutical analysis, a capillary electrophoresis device, an electronic measurement device, and a mass spectroscopy device. More generally, the fluidic device may be applied in any technical application in which an electrically and/or magnetically driven fluid transport mechanism using an external force is implemented.

In the following, further exemplary embodiments of the method for manufacturing the fluidic device will be explained. However, these embodiments also apply to the fluidic device.

The method may comprise depositing the transport medium on the substrate. Such a deposition procedure may denote any procedure on which the transport medium is not only injected in fluid paths formed in a substrate, but in which the transport medium is applied onto at least one surface of a substrate. Particularly, such a deposition technique may include a printing technique, like serigraph, ink-jet, bubble-jet, intaligo, offset printing, thermal laser printing, stamping, varnishing, and dispensing. Printing is very easy, cheap and is properly controllable in a spatial manner so as to make it possible to manufacture the fluidic device with low cost.

The method may comprise providing the transport medium with a material gradient along the substrate, for example by mixing a plurality of components in a spatially dependent manner along an extension of the substrate. For instance, two nozzles or two print heads may provide two or more different components in a spatially dependent manner, thereby making it possible to manufacture a gel gradient transport medium or the like with low effort.

The method may comprise freeze-drying, quick-freezing, or shock-freezing the transport medium before, during or after deposition on the substrate. By performing such procedures, it may be possible to generate a fluidic device which can be stored a long time before being actually used for a fluid analysis experiment. For use, the fluidic device may then be melted, and may additionally be humidified to condition it for subsequent use.

The method may comprise applying a pattern of hydrophilic and hydrophobic portions on the substrate, thereby defining pathways for the fluidic sample when being applied to the fluidic device. When the fluidic sample is based on water (for instance is an aqueous solution), it will be accumulated in hydrophilic portions, and essentially no water will remain in hydrophobic portions. Therefore, by covering different surface portions with different materials may allow to define fluid pathways.

The method may comprise covering at least a part of the transport medium with a passivation layer. This may be performed to protect the transport medium from an undesired external influence.

At least a part of the transport medium covered with the passivation layer may be selectively removed, particularly for making the fluidic device ready for use.

The method may further comprise providing the transport medium on the substrate in a saturated vapor environment. This may allow to manufacture the transport medium with high quality, since drying (which may be preferred in exemplary embodiments) may be suppressed or prevented.

It is also possible that a 'channelless wall' can also be implemented in a 3D structure (like a spider web). For instance, it is possible to use the ultra thin fibers of a spider web as separation paths.

According to an exemplary embodiment, three-dimensional structures can be realized (for example bond-contacts from the gel to electrical contact pads).

According to another exemplary embodiment, a foil may be provided with, for instance, pads with electrical extensions on it. This is foil may be then, on demand, printed with at least one separation channel. With a capillary or any other device will then the sample be injected directly in the fluid (for example 40 pl like the sample plug in existing chips). And then, the sample may be separated with capillary electrophoresis.

Embodiments of the invention are not limited with regard to any specific operation mode, but any driving scheme implementing external forces may be used. The layout of the fluidic structure is variable (2D or 3D). It is possible to provide individual fluid transport structures or complex networks thereof. The fluid transport medium may be entirely active, or may be a mixture of active an passive (inactive) components.

BRIEF DESCRIPTION OF DRAWINGS

Objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
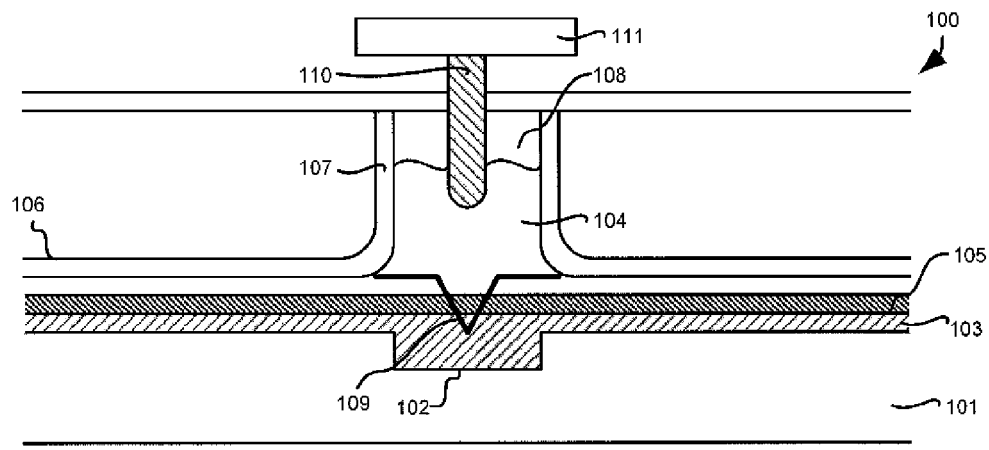
FIG. 1 to FIG. 4 show fluidic devices according to exemplary embodiments of the invention.

The illustration in the drawing is schematically.

In the following, referring to FIG. 1, a fluidic device 100 according to an exemplary embodiment of the invention will be explained.

FIG. 1 shows a cross-sectional view of the fluidic device 100 which is a gel electrophoresis device.

The fluidic device 100 comprises a glass substrate 101 in which a recess 102 has been formed, for instance by etching. A gradient gel strip 103 is deposited as a fluid transport medium on the glass substrate 101 to define a transport path for transporting a fluidic sample 104 driven by an electric force.

Although a central portion of the transport medium 103 is also positioned in the recess 102, the major portion of the transport medium 103 is deposited on a planar surface of the substrate 101 by printing. Therefore, the transport medium 103 is free of a lateral support by the substrate 101 along the major part of a lateral wall of the transport medium 103 (which cannot be seen in FIG. 1).

A passivation layer 105 made of a varnish and having a thickness of for example 1 µm is deposited over an entire surface of the substrate 101 which is partially covered with the transport medium 103. The passivation layer 105 therefore covers the substrate 101 and the transport medium 103.

A carrier element 106 is provided as a mechanical support element and comprises a tubular section 107 defining a well 108. The carrier element 106 can be clicked onto the substrate 101 covered by the transport medium 103 and the passivation layer 105 in a manner to enable external access to the transport medium 103 via the well 108, as will be explained in more detail in the following.

As can further be taken from FIG. 1, a metallic tip or cutting element 109 is foreseen in a lower portion of the carrier element 106 connected to a lower portion of the tubular element 107. It is adapted to penetrate through the passivation layer 105 in the operation state shown in FIG. 1 in which the carrier element 106 is connected to the substrate 101. Thereby, the tip 109 selectively destroys a portion of the passivation layer in an environment of the well 108.

In the tubular section 107, the fluidic sample 104 to be analyzed or examined can be filled in the device 100 using a pipette, a fluid supply needle of an autosampler or of a fractioner, or the like.

The passivation layer 105 may also be made of a water-soluble varnish so that the fluidic sample 104 in contact with the varnish 105 selectively removes the varnish 105 in an area of the tubular well 107.

Furthermore, an electric contact 110 connected to an electric voltage supply unit 111 is dipped in the fluidic sample 104 so as to generate an electric field in the fluid carrying components fluidic device 100. This electric field is needed for performing a gel electrophoresis separation.

The gradient gel 103 adheres to the substrate 101. The gradient gel 103 is further adapted for transporting the fluidic sample 104 driven by an externally applicable electric force generated by the electric contact pin 110 to which an electric voltage is applied by the electric voltage supply unit 111.

The glass substrate 101 is optically transparent so as to enable an optical read out (for instance performing a fluorescence measurements or the like) of different fractions of the fluidic sample which may be separated along an extension of the gradient gel structure 103.

When a sample 104 is filled in the well 108 and is brought in contact—due to the spatially restricted removal of the passivation layer 105 when being contacted with the sample 104—with the elevated gradient gel strip 103, an applied electric force (generated by applying a voltage to the tip 110) will force charged components in the fluidic sample 104 to move along an extension of the gel strip 103, thereby separating different components of the fluidic sample 104. After separation, the different fractions of the fluidic sample 104 may be detected optically (not shown in FIG. 1), for instance by a fluorescence detection arrangement.

In the following, referring to FIG. 2, a cross-sectional view of a fluidic device 200 according to another exemplary embodiment will be explained.

The fluidic device 200 is formed on a glass substrate 101. A first transport medium conduit 201, a second transport medium conduit 202 and a third transport medium conduit 203 which are formed as elongated conduits deposited on top of a surface of the substrate 101 are shown. In a direction perpendicular to the paper plane of FIG. 2, the structures 201 to 203 extend along a dimension which is essentially larger than a cross-sectional dimension in the paper plane of FIG. 2.

The structures 201 to 203 are formed by a printing procedure by moving a print head in a controlled manner along a two-dimensional scanning surface of the substrate 101, selectively depositing gel material for forming the conduits 201 to 203.

The first and the third conduits 201 and 203 are directly applied onto a planar portion of the substrate 101 as non-trenched walls or channelless walls which are free of any lateral mechanical support by the substrate 101. In other words, the channelless wall 204 of the conduits 201 to 203 provide a sufficient degree of mechanical stability of the structures 201 to 203, particularly of the lateral stability of these structures 201 to 203. As can further be taken from FIG. 2, the first and the third conduits 201, 203 are formed on planar portions of the surface 201, whereas the conduit 202 is printed partially in a recess 102 formed in the substrate 101. However, also this second conduit 202 essentially provides the lateral mechanical support by itself, without a need of lateral walls of the recess 102.

Figure 2:
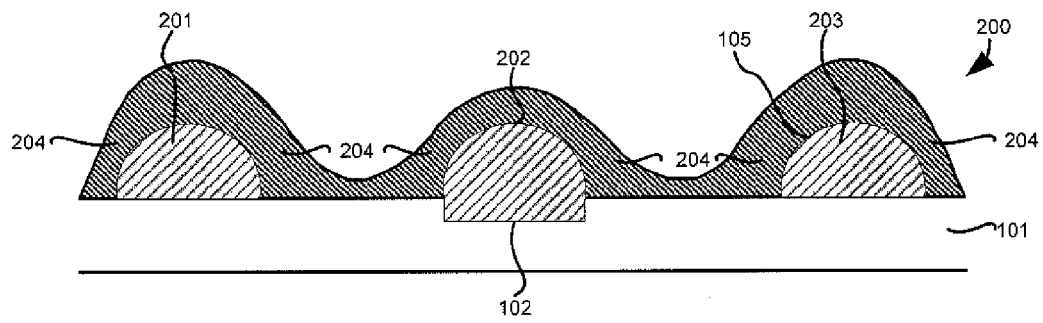

Still referring to FIG. 2, the transport medium structures 201 to 203 are formed by ink-jet printing, whereas the passivation layer 105 is formed as a continuous layer over the surface of the substrate 101 on which the structures 201 to 203 have been deposited. The deposition of the passivation layer 105 may be performed by any planar deposition procedure, like Chemical Vapor Deposition (CVD), Plasma Enhanced Chemical Vapor Deposition (PECVD), or Atomic Layer Deposition (ALD).

Figure 3:
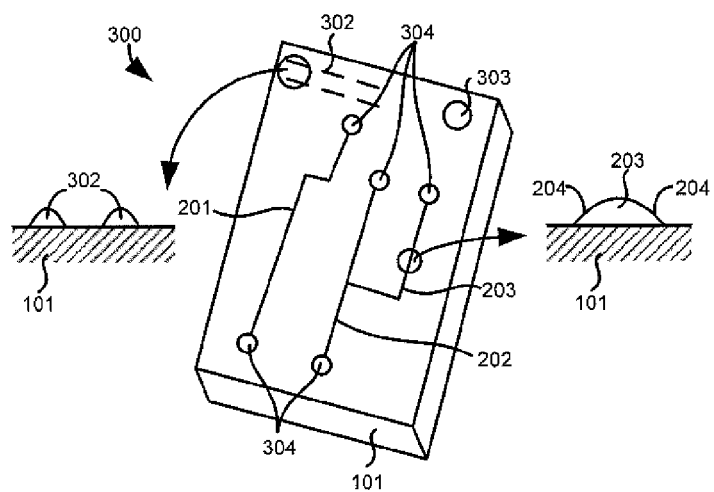

FIG. 3 shows a plan view of a fluidic device 300 according to an exemplary embodiment.

Structures 201 to 203 are shown as well in this plan view, whereas a passivation layer 105 is omitted in the embodiment of FIG. 3.

After having deposited the structures 201 to 203, they are shock-freezed by cooling so as to be brought in a state in which drying of the gel material of the transport medium structures 201 to 203 is avoided or delayed.

Furthermore, first alignment markers 302 shaped as strips and a second alignment marker 303 shaped as a circle are applied to the surface of the substrate 201. The alignment markers 302, 303 serve for positioning the substrate 101 with regard to another substrate (not shown) when these two substrates shall be bonded together, for instance. For this purpose, the alignment markers 302, 303 should be visually inspectable. To provide this function, the structures 302, 303 are printed on the surface of the substrate 101 during the same procedure by which the structures 201 to 203 are printed on the substrate 101. However, the material used for depositing the alignment markers 302, 303 is fluid separation gel which comprises additionally a dye material.

Furthermore, FIG. 3 shows enlarged cross-sectional views of portions of the fluidic device 300.

As can be taken from the enlarged cross-sectional view of the third conduit structure 203, the lateral walls 204 of this conduit 203 are mechanically stable intrinsically without external support, and a lower portion of the gel material is fixedly connected and adheres in a mechanically fixed manner on a surface of the substrate 101.

As can further be taken from the enlarged cross-sectional view of the alignment markers 302, the lateral walls of these alignment markers 302 are mechanically stable intrinsically without external support, and a lower portion of the gel material is fixedly connected and adheres in a mechanically fixed manner on a surface of the substrate 101.

For using the fluidic device 300 for an electrophoresis experiment, it is possible to melt the shock-freezed apparatus 300, and optional to humidify it in order to condition it for an experiment.

In the following, referring to FIG. 4, a fluidic device 400 according to an exemplary embodiment will be explained.

Figure 4:
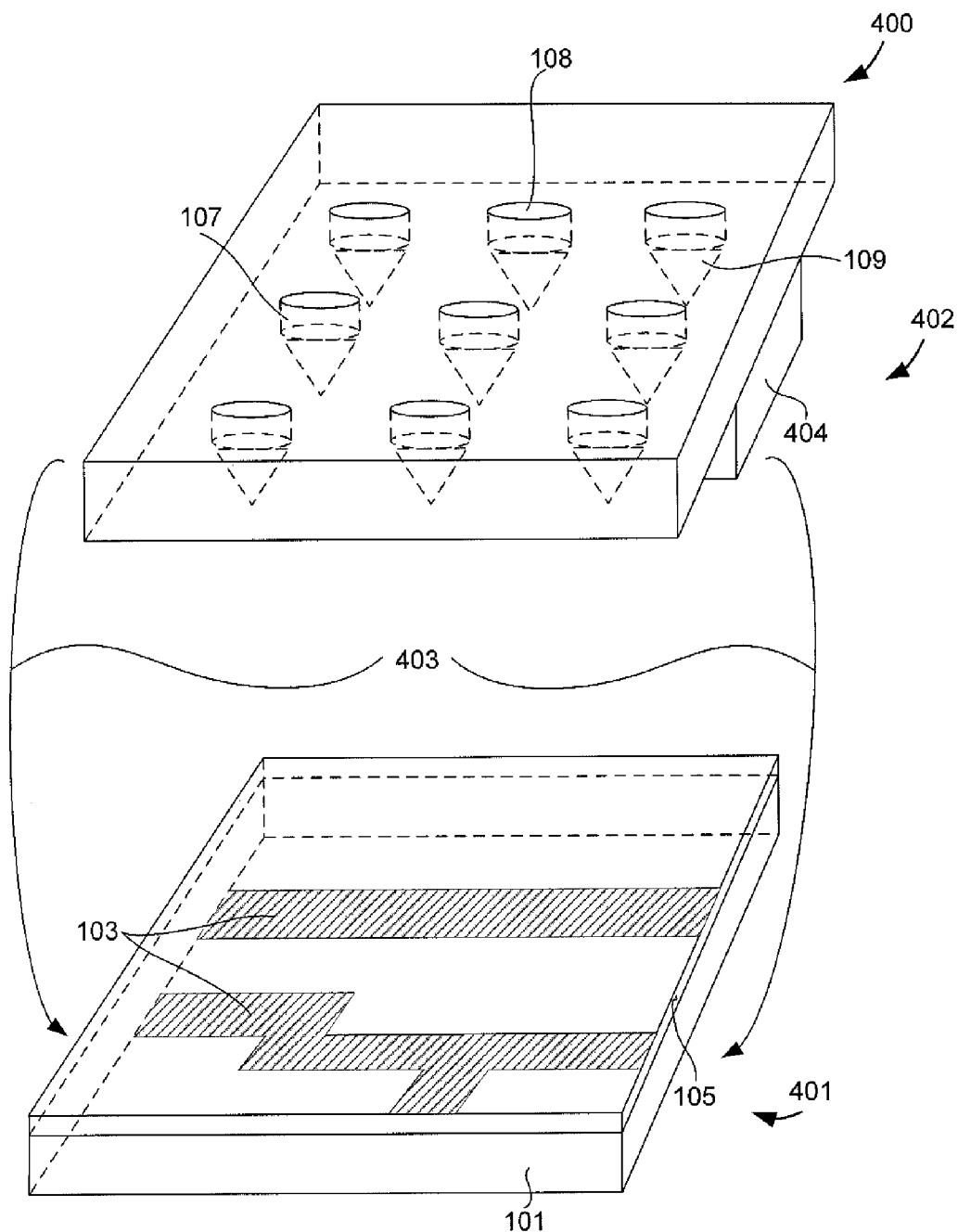

FIG. 4 shows the fluidic device 400 in a partially disassembled state.

It comprises a chip component 401 and a carrier element 402.

The chip component 401 comprises a glass substrate 101 on which two gel structures 103 (one of which is bifurcated) are formed by e.g. printing. On the top of this structure, a passivation layer 105 of a varnish material is deposited.

The carrier element 402 comprises a plurality of wells 108. Each of the wells 108 has an assigned sharp tip or cutting element 109. In a similar manner as shown in FIG. 1, and as indicated by arrows 403, the carrier element 402 can be attached to the chip element 401 by clicking or using a snap-fit connection, which can be promoted by a fastening element 404 which can be brought in alignment with a lower surface of the substrate 101. When a user clicks the carrier element on the chip component 401, the sharp tips 109 automatically penetrate the varnish layer 105. When a fluidic sample is filled in the wells 108, the fluidic sample can be brought in fluid communication with the partially exposed transport medium structures 103.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fluidic device comprising:
a substrate;
a transport medium provided on the substrate and at least partially covered by a passivation layer, wherein the transport medium defines a transport path for transporting a fluidic sample driven by an external force; and
a carrier element having a well, wherein the carrier element is adapted to be connected to the substrate in a manner to enable external access to the transport medium through the well,
wherein the carrier element comprises a tip located and designed to penetrate through the passivation layer when the carrier element is connected to the substrate.

2. The fluidic device of claim 1 wherein
the transport medium comprises a non-trenched wall; or
the transport medium is free of a mechanical support; or
the transport medium is free of a lateral mechanical support by the substrate along at least a part of a lateral wall of the transport medium.

3. The fluidic device of claim 1,
wherein the transport medium comprises a channelless wall.

4. The fluidic device of claim 3, wherein
the channelless wall is defined by an edge portion of the transport medium; or
the channelless wall is formed functionally independently of a sub-surface trench in the substrate.

5. The fluidic device of claim 1, comprising
at least one recess formed in the substrate and being in fluid communication with the transport medium.

6. The fluidic device of claim 1,
wherein the passivation layer comprises at least one material of the group consisting of a varnish, silicone, and a water-soluble material.

7. The fluidic device of claim 1, further comprising
a detachable cover, covering at least a part of the substrate and at least a part of the transport medium.

8. The fluidic device of claim 1, further comprising
at least one alignment marker provided on the substrate and comprising the same material as the transport medium,
wherein the at least one alignment marker additionally comprises a dye material.

9. The fluidic device of claim 1, wherein
the transport medium comprising at least two portions separated from each other by a swellable material which, in a swollen state, enables a fluid communication between the at least two portions via the swollen material, and, in a non-swollen operation state, disables a fluid communication between the at least two portions via the swellable material; or
the transport medium adheres to the substrate; or
the transport medium is adapted for transporting the fluidic sample driven by an electric force; or
wherein the transport medium is adapted for transporting the fluidic sample driven by an externally applicable electric force.

10. The fluidic device of claim 1 wherein
the fluidic device comprises an electric contact to be electrically coupled to the transport medium; or
the fluidic device comprises an electric contact to be electrically coupled to the transport medium via the fluidic sample; or
the transport medium comprises a gel; or
the transport medium comprises a gradient gel or gel like fluid; or
the fluidic device is adapted as a fluidic chip device; or
the fluidic device is adapted as a fluid separation device; or
the fluidic device is adapted as an electrophoresis device; or
the fluidic device is adapted as a gel electrophoresis device; or
the fluidic device is adapted as a microfluidic device; or
the fluidic device is adapted as a nanofluidic device; or
the fluidic device is adapted as a picofluidic device; or
the fluidic device is adapted to transport the fluidic sample comprising at least one of the group consisting of antibodies, a chemical relevant substance, a biological relevant substance, and a dye; or
the fluidic device comprises at least one channel formed in the substrate for channeling the fluidic sample; or
the fluidic device comprises at least one channel formed in the substrate and filled with the transport medium for channeling the fluidic sample, wherein the at least one channel is in fluid communication with the transport medium provided on the substrate; or
the substrate comprises an optical transparent material; or
the substrate comprises at least one material of the group consisting of glass, a semiconductor material, a plastics material, PMMA, a ceramics material and a metallic material; or
the fluidic device is adapted to analyze at least one of the group consisting of a physical, a chemical and a biological parameter of at least one compound of the fluidic sample; or
the fluidic device comprises at least one of a sensor device, a device for chemical, biological and/or pharmaceutical analysis, a capillary electrophoresis device, an electronic measurement device, and a mass spectroscopy device.

11. The fluidic device of claim 1, wherein the passivation layer is selectively removed or destroyed to expose an active surface of the substrate.

* * * * *